(12) United States Patent
Lishchiner et al.

(10) Patent No.: US 11,667,591 B2
(45) Date of Patent: *Jun. 6, 2023

(54) METHODS FOR PRODUCING AROMATIC HYDROCARBONS FROM NATURAL GAS AND PROCESSING UNIT FOR IMPLEMENTING SAME

(71) Applicant: NGT Global AG, Zug (CH)

(72) Inventors: Iosif Izrailevich Lishchiner, Moscow (RU); Olga Vasilyevna Malova, Moscow (RU); Andrey Leonidovich Tarasov, Moscow (RU); Vladimir Vladislavovich Imshenetskiy, Moscow (RU); Sergey Vladimirovich Medvedev, Gorki Leninskie (RU); Denis Vasilyevich Pchelintsev, Moscow (RU)

(73) Assignee: NGT Global AG, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/780,788

(22) Filed: Feb. 3, 2020

(65) Prior Publication Data

US 2020/0283353 A1    Sep. 10, 2020

Related U.S. Application Data

(63) Continuation-in-part of application No. 15/113,141, filed as application No. PCT/RU2015/000024 on Jan. (Continued)

(30) Foreign Application Priority Data

Jan. 22, 2014  (RU) ............................ RU2014101936
Jan. 28, 2014  (RU) ............................ RU2014102625
(Continued)

(51) Int. Cl.
  C07C 2/86        (2006.01)
  C10G 35/06       (2006.01)
  (Continued)

(52) U.S. Cl.
  CPC ............... *C07C 2/864* (2013.01); *B01J 21/04* (2013.01); *B01J 21/08* (2013.01); *B01J 29/061* (2013.01);
  (Continued)

(58) Field of Classification Search
  CPC ........................................................ C07C 1/20
  See application file for complete search history.

(56) References Cited

U.S. PATENT DOCUMENTS 3,763,205 A * 10/1973  Green .................... C07C 31/04
                                                        518/704
6,375,916 B2 * 4/2002  Christensen ............ C01B 3/382
                                                        423/418.2
(Continued)

FOREIGN PATENT DOCUMENTS

RU    2189858 C1 *  9/2002  ............... C07C 1/20
RU    2284343 C1 *  9/2006  ........... C10G 35/095

OTHER PUBLICATIONS

Machine translation RU2284343. Retrieved Dec. 31, 2020 (Year: 2020).*

(Continued)

*Primary Examiner* — Philip Y Louie
*Assistant Examiner* — Alyssa L Cepluch
(74) *Attorney, Agent, or Firm* — Glen P. Belvis; Belvis Law, LLC.

(57) ABSTRACT

The invention relates to the field of gas chemistry and, more specifically, to methods and devices for producing aromatic hydrocarbons from natural gas, which involve producing
(Continued)

Figure 1:
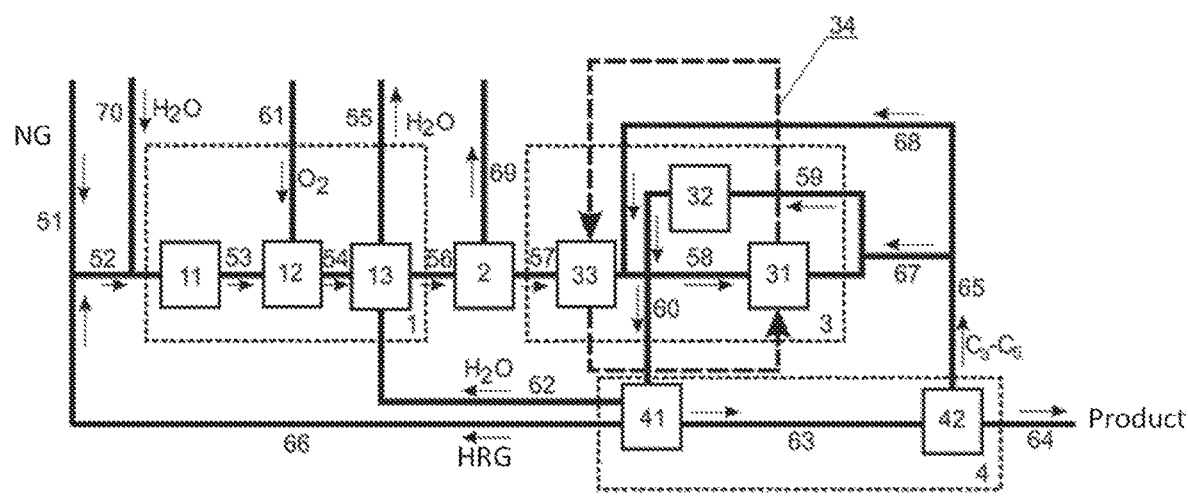

synthesis gas, converting same into methanol producing, from the methanol, in the presence of a catalyst, a concentrate of aromatic hydrocarbons and water, separating the water, air stripping hydrocarbon residues from the water, and separating-out the resultant concentrate of aromatic hydrocarbons and hydrogen-containing gas, the latter being at least partially used in the production of synthesis gas to adjust the ratio therein of $H_2$:CO 1.8-2.3:1, and can be used for producing aromatic hydrocarbons. According to the invention, the production of aromatic hydrocarbons from methanol in the presence of a catalyst is carried out in two consecutively-connected reactors for synthesizing aromatic hydrocarbons: in a first, low-temperature isothermal reactor for synthesizing aromatic and aliphatic hydrocarbons, and in a second, high-temperature adiabatic reactor for synthesizing aromatic and aliphatic hydrocarbons from aliphatic hydrocarbons formed in the first reactor, and the subsequent stabilization thereof in an aromatic hydrocarbon concentrate stabilization unit. At least a portion of the hydrogen-containing gas is fed to a synthesis gas production unit and is used for producing synthesis gas using autothermal reforming technology. The installation carries out the method. The achieved technical result consists in increasing the efficiency of producing concentrates of aromatic hydrocarbons.

7 Claims, 1 Drawing Sheet

Related U.S. Application Data 20, 2015, now Pat. No. 10,550,045, application No. 16/780,788 is a continuation-in-part of application No. 16/195,022, filed on Nov. 19, 2018, now Pat. No. 10,894,752, which is a continuation of application No. 15/113,147, filed as application No. PCT/RU2014/000953 on Dec. 17, 2014, now Pat. No. 10,131,592, application No. 16/780,788 is a continuation-in-part of application No. 15/129,662, filed as application No. PCT/RU2015/000171 on Mar. 25, 2015, now Pat. No. 10,550,331, application No. 16/780,788 is a continuation-in-part of application No. 15/502,956, filed as application No. PCT/RU2015/000496 on Aug. 10, 2015, now Pat. No. 10,556,846.

(30) Foreign Application Priority Data

Mar. 28, 2014 (RU) .......................... RU2014111985
Aug. 14, 2014 (RU) .......................... RU2014133053

(51) Int. Cl.
| | |
|---|---|
| *C07C 1/20* | (2006.01) |
| *B01J 29/80* | (2006.01) |
| *B01J 21/04* | (2006.01) |
| *B01J 21/08* | (2006.01) |
| *B01J 29/40* | (2006.01) |
| *B01J 35/00* | (2006.01) |
| *B01J 37/04* | (2006.01) |
| *B01J 37/30* | (2006.01) |
| *B01J 29/06* | (2006.01) |

(52) U.S. Cl.
CPC ............ *B01J 29/40* (2013.01); *B01J 29/405* (2013.01); *B01J 29/80* (2013.01); *B01J 35/0006* (2013.01); *B01J 37/04* (2013.01); *B01J 37/30* (2013.01); *C07C 1/20* (2013.01); *C10G 35/065* (2013.01); *B01J 2029/062* (2013.01); *B01J 2219/00051* (2013.01); *B01J 2229/183* (2013.01); *B01J 2229/38* (2013.01); *C07C 2521/04* (2013.01); *C07C 2521/08* (2013.01); *C07C 2529/40* (2013.01); *C07C 2529/80* (2013.01); *C10G 2300/104* (2013.01); *C10G 2300/1044* (2013.01); *C10G 2400/30* (2013.01)

(56) References Cited

U.S. PATENT DOCUMENTS 6,455,747 B1 * 9/2002 Lattner ................... C10G 3/60
585/638
2011/0152594 A1 * 6/2011 Brown ..................... C10G 3/54
585/408

OTHER PUBLICATIONS

Machine translation RU2189858. Retrieved Dec. 31, 2020 (Year: 2020).*

* cited by examiner

METHODS FOR PRODUCING AROMATIC HYDROCARBONS FROM NATURAL GAS AND PROCESSING UNIT FOR IMPLEMENTING SAME

This application is: (i) a continuation-in-part of U.S. application Ser. No. 15/113,141 filed Jul. 21, 2016, which is a US nationalization pursuant to 35 U.S.C. § 371 of PCT/RU2015/000024 filed Jan. 20, 2015, which claims priority to RU Patent Application Serial No. 2014101936, filed Jan. 22, 2014; (ii) is a continuation-in-part of 16/195,022 filed Nov. 19, 2018, which is a continuation of Ser. No. 15/113,147 filed Jul. 21, 2016, which is a US nationalization pursuant to 35 U.S.C. § 371 of PCT/RU2014/000953 filed Dec. 17, 2014, which claims priority to RU Patent Application Serial No. 2014102625, filed Jan. 28, 2014; (iii) is a continuation-in-part of Ser. No. 15/129,662 filed Sep. 27, 2016 which is a US nationalization pursuant to 35 U.S.C. § 371 of PCT/RU2015/000171 filed Mar. 25, 2015, which claims priority to RU Patent Application Serial No. 2014111985, filed Mar. 28, 2014; and (iv) a continuation-in-part of U.S. patent application Ser. No. 15/502,956 filed Feb. 9, 2017, which is a US nationalization pursuant to 35 U.S.C. § 371 of PCT/RU2015/000496 filed Aug. 10, 2015, which claims priority to RU Patent Application Serial No. 2014133053, filed Aug. 12, 2014, the entire disclosures of each of which are incorporated herein by reference.

THE FIELD OF THE INVENTION

The invention relates to the field of gas chemistry, and more specifically to methods and devices for producing aromatic hydrocarbons from natural gas, which involve producing synthesis gas, converting the same into methanol, producing, from the methanol, in the presence of a catalyst, a concentrate of aromatic hydrocarbons and water, separating the water, air stripping hydrocarbon residues from the water, and separating-out the resultant concentrate of aromatic hydrocarbons and hydrogen-containing gas, the latter being at least partially used in the production of synthesis gas to adjust the ratio therein of $H_2:CO$ 1.8-2.3:1, and can be used for producing aromatic hydrocarbons.

It should be noted that hereinafter the term methanol is also used to refer to a mixture of methanol and dimethyl ether because dimethyl ether would also be formed in a reactor and the synthesis does not only occur with methanol, but also with dimethyl ester.

Aromatic hydrocarbons, particularly benzene, toluene, ethylbenzene and xylenes, are important chemical products which are mass-produced in the petrochemical industry. Currently, aromatic compounds are usually produced by various methods from starting materials based on crude oil, including catalytic reforming and cracking. However, there is an increasing need to find alternative sources of aromatic hydrocarbons as world supplies of starting materials based on crude oil diminish.

One possible alternative source for producing aromatic hydrocarbons is methane, which is a base component of natural gas and biogas. Due to the problems associated with transporting large quantities of natural gas, most natural gas extracted with petroleum, particularly in remote places, is flared. Therefore, converting alkanes contained in natural gas directly to higher molecular weight hydrocarbons, such as aromatics, is a particularly attractive method for upgrading natural gas provided that the technical difficulties accompanying said conversion can be overcome.

Most methods for converting methane to liquid hydrocarbons involve first converting methane to synthesis gas, a mixture of hydrogen and carbon oxides (CO and/or $CO_2$). The production of synthesis gas is expensive and energy intensive. However, methods for producing aromatic compounds that involve simultaneously producing synthesis gas are particularly attractive because synthesis gas may have a high value. Synthesis gas has a high potential value because it may be used in subsequent reactions to form methanol, higher alcohols, acetic acid, ammonia, acetone, acetaldehyde, ethylene oxide, ethylene glycol, dimethyl ether, and petrol having linear alkanes and/or alkenes. Producing such a wide variety of products is preferable because these chemicals are worth more than methane and they are easier to transport for sale.

PRIOR ART

The present invention first relates to a method for producing a concentration of aromatic hydrocarbons from natural gas, which involves producing synthesis gas, converting same to methanol, producing, from the methanol, in the presence of a catalyst, a concentrate of aromatic hydrocarbons and water, separating the water, air stripping hydrocarbon residues from the water, and separating-out the resultant concentrate of aromatic hydrocarbons and hydrogen-containing gas, the latter being at least partially used in the production of synthesis gas to adjust the ratio therein of $H_2:CO$ 1.8-2.3:1.

Such a method is described in the Russian Patent No. 2362760 published in 2009.

This method is the closest in terms of technological essence and the technical result to be achieved, and is selected as the prior art for the proposed invention.

The disadvantage of this prior art is the inefficiency in the production of concentrates of aromatic hydrocarbons. This occurs due to the fact that a large quantity of product is lost as by-products.

DISCLOSURE OF THE INVENTION AS A METHOD

The present invention, which relies on this original observation, mostly aims to provide a method for producing aromatic hydrocarbons from natural gas, which makes it possible to overcome at least one of the above-mentioned disadvantages.

In order to achieve this goal, the production of aromatic hydrocarbons from methanol in the presence of a catalyst is carried out in two consecutively-connected reactors for synthesizing aromatic hydrocarbons: in a first, low-temperature isothermal reactor for synthesizing aromatic and aliphatic hydrocarbons, and in a second, high-temperature adiabatic reactor for synthesizing aromatic and aliphatic hydrocarbons from aliphatic hydrocarbons formed in the first reactor, and the subsequent stabilization of the concentrate of aromatic hydrocarbons in a stabilization unit. At least a portion of the hydrogen-containing gas is used for producing synthesis gas using autothermal reforming technology with a pre-reforming unit or non-catalytic partial oxidation using oxygen or oxygen-air mixtures as the oxidant to adjust the ratio therein according to the relationship: (the MF of $H_2$–the MF of $CO_2$)/(the MF of CO+the MF of $CO_2$)≥2, where MF stands for the mole fraction of the component in the synthesis gas.

This advantage makes it possible to improve efficiency in the production of concentrates of aromatic hydrocarbons due to the fact that the aliphatic hydrocarbons produced in the first reactor for synthesizing aromatic hydrocarbons are additionally processed in the second reactor for synthesizing aromatic and aliphatic hydrocarbons, wherein the treatment process is carried out at a higher temperature. Using a portion of the hydrogen-containing gas to produce synthesis gas enables the possibility of providing for an increase in the yield of methanol as an intermediate raw ingredient and consequently, an increase in the yield of aromatic hydrocarbons.

The invention comprises a variant in which the reaction zone of the first reactor for synthesizing aromatic and aliphatic hydrocarbons is thermally stabilized by heating an external agent, wherein the heat is removed from the external agent by evaporating methanol in a methanol evaporator mounted between the methanol synthesizing unit and the first, low-temperature isothermal reactor for synthesizing aromatic and aliphatic hydrocarbons.

This advantage makes it possible to cool the first, low-temperature isothermal reactor for synthesizing aromatic and aliphatic hydrocarbons.

The invention comprises a variant in which light aliphatic hydrocarbons to be removed from the converted product in a separating unit are at least partially fed to the reaction zone of the first low-temperature isothermal reactor for synthesizing aromatic and aliphatic hydrocarbons and/or to the reaction zone of the second high-temperature adiabatic reactor for synthesizing aromatic and aliphatic hydrocarbons, which provides for an increase in the yield of concentrate of aromatic hydrocarbons.

This advantage makes it possible to additionally increase the useful yield of concentrate of aromatic hydrocarbons, thereby reducing the quantity of light aliphatic hydrocarbons to be removed from the discharge gases due to the recycling thereof.

The invention comprises a variant in which a catalyst based on a pentasil-type crystalline aluminosilicate with $SiO_2/Al_2O_3=25$-$100$ is used as the catalyst of the first low-temperature isothermal reactor for synthesizing aromatic and aliphatic hydrocarbons, which comprises 0.05-0.1 wt. % sodium oxide, in which zinc oxides, rare earth oxides and a binding component are additionally included in the following ratio of components, wt. %:
  zinc oxide: 0.5-3.0,
  rare earth oxides: 0.1-5.0,
  cobalt oxide: 0.05-2.5,
  crystalline aluminosilicate: 63-70, and
  binder: the remainder.

This advantage makes it possible to improve the performance of the catalyst, specifically to enhance the mechanical strength of granules and to improve its capability for oxidative regeneration.

The invention comprises a variant in which a catalyst based on a pentasil-type crystalline aluminosilicate with $SiO_2/Al_2O_3=25$-$120$ is used as the catalyst of the second high-temperature adiabatic reactor for synthesizing aromatic and aliphatic hydrocarbons, which comprises 0.05-0.1 wt. % sodium oxide, in which zinc oxides, sodium oxide, rare earth oxides and a binding component are additionally included in the following ratio of components, wt. %:
  zinc oxide: 0.5-3.0,
  sodium oxide: 0.12-0.30,
  rare earth oxides: 0.1-3.0,
  cobalt oxide: 0.05-2.5,
  crystalline aluminosilicate: 63.0-70.0, and
  binder: the remainder,
  wherein the composition of the rare earth oxides is:
  cerium oxide $CeO_2$: 3.0,
  lanthanum oxide $La_2O_3$: 65.0,
  neodymium oxide $Nd_2O_3$: 21.0,
  praseodymium oxide $Pr_6O_{11}$: the remainder.

This advantage makes it possible to improve the performance of the catalyst, specifically to enhance the mechanical strength of granules and to improve its capability for oxidative regeneration.

There is a variant of the invention in which the hydrogen-containing gas produced in the process of synthesizing and separating the concentrate of aromatic hydrocarbons, when necessary, is used in the process of hydrogenating sulfur-containing compounds, the removal of which preferably occurs using a step of hydrogenating to hydrogen sulfide.

This advantage makes it possible to reuse the hydrogen-containing gas produced in the unit for separating the conversion product in the process for hydrogenating sulfur-containing compounds.

The invention comprises a variant in which, together with the hydrogenation of sulfur-containing compounds to hydrogen sulfide, in one reactor, olefins which are contained in the produced hydrogen-containing gas are hydrogenated, which prevents the formation of carbonaceous deposits on the surface of the hydrogen sulfide chemisorbent and on the surface of the pre-reforming catalyst used to stabilize the component composition and to reduce the steam/carbon ratio in the steam-gas mixture to be converted to synthesis gas.

This advantage makes it possible to prevent the formation of carbonaceous deposits on the surface of the hydrogen sulfide chemisorbent and on the surface of the pre-reforming catalyst, as well as an opportunity to stabilize the component composition and to reduce the steam/carbon ratio in the steam-gas mixture to be converted to synthesis gas.

The combination of significant features of the proposed invention is not known from the prior art for methods having a similar purpose, which makes it possible to reach the conclusion that the invention as a method satisfies the criterion of novelty.

The Prior Art for the Processing Unit

Another aspect of the present invention relates to a processing unit for producing a concentrate of aromatic hydrocarbons from natural gas, which includes the following consecutively connected elements: a unit for producing synthesis gas, a unit for producing methanol, a unit for producing a concentrate of aromatic hydrocarbons and a unit for separating the conversion product into reaction water, discharge hydrogen-containing gas, a fraction of light aliphatic hydrocarbons, and a stable concentrate of aromatic hydrocarbons, which is connected to a unit for producing the synthesis gas.

Such a processing unit is described in Russian Patent No. 2362760 which was published in 2009.

This processing unit is the closest in terms of technological essence and the technical result to be achieved, and is selected as the prior art for the proposed invention.

The disadvantage of this prior art is the inefficiency in the production of concentrates of aromatic hydrocarbons. This occurs due to the fact that a large quantity of product is lost as by-products.

Disclosure of the Invention as a Processing Unit

The main aim of the present invention is to provide a processing unit for producing a concentrate of aromatic hydrocarbons from natural gas, which includes the following consecutively connected elements: a unit for producing synthesis gas, a unit for producing methanol, a unit for producing a concentrate of aromatic hydrocarbons and a unit for separating the conversion product into reaction water, discharge hydrogen-containing gas, a fraction of light aliphatic hydrocarbons and a stable concentrate of aromatic hydrocarbons, which is connected to the unit for producing the synthesis gas and to the unit for producing aromatic hydrocarbons, which makes it possible to overcome at least one of the above-mentioned disadvantages.

In order to achieve this goal, the unit for producing a concentrate of aromatic hydrocarbons comprises two consecutively-connected reactors for synthesizing aromatic hydrocarbons: a first, low-temperature isothermal reactor for synthesizing aromatic and aliphatic hydrocarbons, and a second, high-temperature adiabatic reactor for synthesizing aromatic and aliphatic hydrocarbons from aliphatic hydrocarbons formed in the first reactor. The processing unit comprises a unit for stabilizing the concentrate of aromatic hydrocarbons. An outlet for the hydrogen-containing gas of the unit for separating the conversion product is connected to an inlet of the unit for producing the synthesis gas.

This advantage makes it possible to improve efficiency in the production of concentrates of aromatic hydrocarbons due to the fact that the aliphatic hydrocarbons produced in the first reactor for synthesizing aromatic hydrocarbons are additionally further treated in the second reactor for synthesizing aromatic and aliphatic hydrocarbons, wherein the treatment process occurs at a higher temperature.

There is a variant of the invention in which the unit for producing the concentrate of aromatic hydrocarbons additionally comprises a recuperative heater for vapors of the crude methanol produced in the methanol synthesis reactor (not shown in the figure).

This advantage makes it possible to remove heat from the conversion products of the second high-temperature reactor for synthesizing aromatic and aliphatic hydrocarbons, using this heat to overheat the methanol vapors at the methanol evaporator outlet.

The invention comprises a variant in which the first low-temperature isothermal reactor for synthesizing aromatic and aliphatic hydrocarbons additionally comprises a circuit with an external heat carrier connected to the methanol evaporator mounted between the unit for synthesizing methanol and the first low-temperature isothermal reactor for synthesizing aromatic and aliphatic hydrocarbons.

This advantage makes it possible to remove heat from the first low-temperature isothermal reactor for synthesizing aromatic and aliphatic hydrocarbons due to the circuit with the external heat carrier, using this heat to evaporate the methanol.

The invention comprises a variant in which the unit for producing the concentrate of aromatic hydrocarbons additionally includes an additional flow heater which is needed to initialize the conversion process of propane and other aliphatic carbohydrates in the conversion product, wherein the temperature of the flow at the heater outlet is at least 30° C. higher than the maximum temperature in the reaction zone of the first reactor.

This advantage makes it possible to initiate the process of converting propane and other aliphatic hydrocarbons in the conversion product.

The invention comprises a variant in which an outlet of the unit for separating the conversion product, through which the light aliphatic hydrocarbons are discharged, is connected to the reaction zone of the first low-temperature isothermal reactor for synthesizing aromatic and aliphatic hydrocarbons and/or to the reaction zone of the second high-temperature adiabatic reactor for synthesizing aromatic and aliphatic hydrocarbons.

This advantage makes it possible to additionally increase the useful yield of the concentrate of aromatic hydrocarbons, thereby reducing the quantity of light aliphatic hydrocarbons to be removed from the discharge gases due to the recycling thereof.

Therefore, the problem addressed in this invention is that of providing for an improvement in the efficiency of the production of concentrates of aromatic hydrocarbons. The problem of interest is solved with the aid of the above-mentioned features.

The combination of significant features of the proposed invention is not known from the prior art for devices which have a similar purpose, which makes it possible to conclude that the invention as a processing unit fulfills the criterion of novelty.

A SHORT DESCRIPTION OF THE DRAWINGS

Figure 2:

The other distinguishing features and advantages of the invention clearly follow from the description given above as a form of illustration and are not limiting with references to the attached drawings in which:

FIG. 1 is a schematic perspective view of the processing unit for producing aromatic hydrocarbons from natural gas, according to the invention, and FIG. 2 schematically shows the steps of the method for producing aromatic hydrocarbons from natural gas, according to the invention.

According to FIG. 1, the processing unit for producing a concentrate of aromatic hydrocarbons from natural gas includes the following consecutively connected elements: a unit (1) for producing synthesis gas, a unit (2) for producing methanol, a unit (3) producing a concentrate of aromatic hydrocarbons and a unit (4) for separating the conversion product into reaction water, discharge hydrogen-containing gas, a fraction of light aliphatic hydrocarbons, and a stable concentrate of aromatic hydrocarbons, which is connected to the unit (1) for producing synthesis gas and the unit (3) for producing a concentrate of aromatic hydrocarbons.

The unit (3) for producing a concentrate of aromatic hydrocarbons comprises two consecutively-connected reactors for synthesizing aromatic hydrocarbons: a first, low-temperature isothermal reactor (31) for synthesizing aromatic and aliphatic hydrocarbons, and a second, high-temperature adiabatic reactor (32) for synthesizing aromatic and aliphatic hydrocarbons from aliphatic hydrocarbons formed in the first reactor (31).

The unit (4) for separating the conversion product into reaction water, discharge hydrogen-containing gas, a fraction of light aliphatic hydrocarbons, and a stable concentrate of aromatic hydrocarbons comprises a unit (41) for condensing the hydrocarbons and reaction water, disposing of the waste water and separating out the hydrogen-containing gas and unstabilized concentrate of aromatic hydrocarbons, and a unit (42) for stabilizing the concentrate of aromatic hydrocarbons (connected by line (63) to unit (41)).

The unit (3) for producing a concentrate of aromatic hydrocarbons additionally comprises a recuperative evaporator (33) for recovering the methanol obtained in the methanol synthesis reactor (2) and a recuperative heater (not shown on FIG. 1) for the crude methanol vapors of the reaction medium from unit (32), which is situated on line (58) between the crude methanol evaporator (33) and the first, low-temperature synthesis reactor (31).

The first, low-temperature isothermal reactor (31) for synthesizing aromatic and aliphatic hydrocarbons additionally comprises a circuit (34) with an external heat carrier connected to the methanol evaporator (33) mounted between the methanol synthesis unit (2) and the first, low-temperature isothermal reactor (31) for synthesizing aromatic and aliphatic hydrocarbons.

The unit (3) for producing a concentrate of aromatic hydrocarbons additionally comprises an additional flow heater (positioned on the line 59) which is needed to initialize the conversion process of propane and other aliphatic hydrocarbons in the conversion product (not shown in FIG. 1).

The outlet of the unit (42) (line 65) for stabilizing the concentrate of aromatic hydrocarbons, through which the light aliphatic hydrocarbons are discharged, is connected to the reaction zone of the first low-temperature isothermal reactor (31) for synthesizing aromatic and aliphatic hydrocarbons (line 68) and/or to the reaction zone of the second high-temperature adiabatic reactor (32) for synthesizing aromatic and aliphatic hydrocarbons (line 67).

The unit (1) for producing the synthesis gas consists of an autothermal reforming unit (12) with an adiabatic pre-reforming unit (11) and a heat recovery unit (13). These are found on lines (52), (53), (54) and (56).

The adiabatic pre-reforming unit (11) is an adiabatic reactor in which processes of destructive hydrogenation and steam conversion of hydrocarbons $C_2$+ occur to form thermally stable compounds $C_1$, CO, and $CO_2$, which makes it possible to increase the heating temperature of the steam-gas mixture before feeding same to the autothermal reforming unit (12), and to reduce the steam/carbon ratio in the steam-gas mixture. A mixture composed of natural gas (fed along line (51)), hydrogen-containing gas (fed along line (66)) and superheated steam (fed along line (70)) is fed to the inlet of unit (11). Before being fed to unit (11), the mixture is superheated to a temperature of 300-450° C.

The autothermal reforming unit (12) is a separate apparatus which blows oxygen along line (61). The main advantage of autothermal reforming is to exclude the step of tubular steam conversion and the possibility of operating with a very low steam/carbon ratio. This enables the production of crude methanol with a methanol concentration of at least 94%, which is suitable for converting into a concentrate of aromatic hydrocarbons without a concentration step. In addition, the lack of hydrogen (in a ratio required for synthesizing methanol) in synthesis gas produced by autothermal reforming is fully compensated by the addition, to the raw material to be converted, of hydrogen-containing discharge gas from the synthesis of the concentrate of aromatic hydrocarbons, and also, when necessary, by the addition, to the synthesis gas (line (56)) of hydrogen removed from the discharge gases from synthesizing methanol (line (69)).

Recycling hydrogen-containing gas from the conversion product separating unit (41) makes it possible to increase the function:

$$f = (\text{the MF of } H_2 - \text{the MF of } CO_2)/(\text{the MF of } CO + \text{the MF of } CO_2)$$

from 1.7-1.9 to the required 2.05-2.1 with a low steam/carbon ratio which reduces the amount of energy lost and the size of the heat exchangers used.

The hydrogen-containing gas is blown from the methanol synthesis unit (2) through line (69).

Water is fed from the conversion product separating unit (41) through line (62) to the heat recovery unit (13). The superheated steam is drawn from the heat recovery unit (13) along line (55).

The superheated steam is fed along line (70) for the production of the steam and gas mixture to be fed to unit (11).

Implementation of the Invention

According to the invention, aromatic hydrocarbons are produced from natural gas in the following manner.

Step A1. The Production of Synthesis Gas

Natural gas (denoted as NG in FIG. 1) is fed to a synthesis gas production unit (1) along lines (51) and (52). In order to produce synthesis gas with the stoichiometric ratio between $H_2$, CO and $CO_2$ required for methanol synthesis, a scheme for producing synthesis gas is used in a process of autothermal reforming or oxygen blowing, in which oxygen is used for the partial and complete oxidation of the carbon in natural gas, wherein, as is known, during the conversion of natural gas by said gases, it is possible to obtain synthesis gas with the stoichiometric ratio:

$f = (\text{the MF of } H_2 - \text{the MF of } CO_2)/(\text{the MF of } CO + \text{the MF of } CO_2)$ less than 1.8, and synthesizing methanol through a circulation scheme requires synthesis gas with $f \geq 2.05$.

Due to the fact that hydrogen-containing gas (denoted in FIG. 1 as HRG) is additionally fed to the unit for producing synthesis gas from the step for synthesizing the concentrate of aromatic hydrocarbons from unit (4) along line (66), synthesis gas with the required stoichiometric ratio $f \geq 2.05$ would be at the outlet of the unit for producing synthesis gas (1), wherein the discharge hydrogen-containing gas from the synthesis of the concentrate of aromatic hydrocarbons is fully recycled, which increases the thermal efficiency coefficient of the integrated process.

Since a steam reformer is not used to correct the composition of the synthesis gas, the content of $CO_2$ in the synthesis gas is small, which enables the production of crude methanol with a concentration of at least 94 wt. %, which makes it possible to eliminate the step of concentrating the crude methanol.

Step A2. Synthesizing Methanol

Afterwards the synthesis gas is fed along line (56) to the methanol synthesis unit (2) where same is converted to crude methanol and discharge synthesis gases which are not shown in the figure and is sent to the methanol evaporator (33) along line (57).

Step A3. Synthesizing the Concentrate of Aromatic Hydrocarbons

The crude methanol from the methanol synthesizing unit (2) enters lines (57), (58), (59) and (60) of unit (3) for synthesizing the concentrate of aromatic hydrocarbons, which is composed of units for evaporating methanol (33), a recuperative heater for the crude methanol vapors (not shown in FIG. 1), the first, low-temperature isothermal reactor (31) for the synthesis of aromatic and aliphatic hydrocarbons, and an additional heater for the conversion product which initiates the conversion of propane and other aliphatic hydrocarbons in the second, high-temperature adiabatic reactor (32) of crude methanol (not shown in FIG. 1) and the second, high-temperature adiabatic reactor (32) for the synthesis of aromatic and aliphatic hydrocarbons from the aliphatic hydrocarbons formed in the first reactor (31).

In addition, the temperature in the first reactor is kept within the range 450°+/−30° C., and in the second reactor the temperature is kept within the range 500°+/−50° C. The pressure in reactors (31) and (32) is from 0.7 to 3 MPa.

Step A4. Heat Removal

Heat is removed from reactor (31) by evaporating methanol in unit (33), and due to the presence of the circuit (34). It is not possible to directly use a methanol evaporator because the critical temperature for methanol is 242° C. An intermediate heat carrier is used for heat removal, the composition of which depends on the type of reactor equipment used in unit (31). Thus, when using a tube reactor cooled by a liquid medium, the heat carrier can be a high-temperature heat carrier based on, for example, dialkylbenzenes or heat carriers based on silicon compounds, molten salts, etc. Furthermore, some of the heat is removed from the heat carrier in the methanol evaporation unit (33).

When using a tube reactor of a eutectic composition to be cooled by a lead-bismuth alloy, heat exchange takes place due to the convective motion of the melt between the reaction tubes and the tubular methanol evaporator.

When using a reactor with an immovable catalyst layer with heat removal using heat tubes, both sodium and heat resistant hydrocarbons can be used as an intermediate heat carrier.

Methanol in a gaseous state can also be used as an intermediate heat carrier.

The circuit for circulating the intermediate heat carrier is denoted by a dotted line in the scheme and by the number 34.

Converting methanol into a concentrate of aromatic hydrocarbons results in the formation of aliphatic hydrocarbons $C_2+$ in addition to said aromatic hydrocarbons, wherein a portion of said aliphatic hydrocarbons $C_2+$ (propane) is converted to aromatic hydrocarbons at high temperatures. In order to convert same, the steam-gas mixture of reactor unit (31) is heated to a temperature of 480-530° C. and fed to reactor (32).

Step A5. Removing Water and Hydrogen-Containing Gas

Afterwards, the mixture from the reactor (32) is fed along line (60) to the unit (41) for separating the conversion product, where the reaction water from the discharge gases is condensed and removed through line (62), hydrogen-containing gas is removed through line (66) and the concentrate of aromatic hydrocarbons is removed through line (63), which enters the stabilization unit (42).

The reaction water to be condensed and separated in the conversion product separation unit (41) is fed to a heat recovery boiler (13). The reaction water is recycled in this manner.

The additional two-stage conversion in reactors (31) and (32) and the reduced temperature in reactor (31) make it possible to reduce the methanol conversion to carbon oxides, which makes it possible to use the discharge hydrogen-containing gas without removing $CO_2$ therefrom to hydrogenate the sulfur-containing compounds in natural gas, thereby improving the functional of synthesis gas to the optimal values. Hydrogen-containing gas contains very little CO or $CO_2$, which partially methanate sulfur-containing compounds on a hydrogenating catalyst, which leads to the formation of steam that reduces the chemisorption ability of zinc oxide or iron oxide.

Step A6. Stabilizing the Concentrate of Aromatic Hydrocarbons

The concentrate of aromatic hydrocarbons is fed through line (63) from the unit (41) for separating the conversion product to a stabilization unit (42), where the gases from the stabilization of the concentrate of aromatic hydrocarbons are also used to convert to a concentrate of aromatic hydrocarbons, wherein said gases are sent through lines (65), (67) and (65), (68) to reactors (31) and (32). The product (denoted in FIG. 1 as Product) is discharged through line (64).

The sequence of steps is an example and makes it possible to rearrange, add or produce various operations at the same time without losing the ability to produce a concentrate of aromatic hydrocarbons from natural gas.

INDUSTRIAL APPLICABILITY

The proposed processing unit for producing a concentrate of aromatic hydrocarbons from natural gas can be implemented by a person skilled in the art in practice, and when implemented, provides for the execution of the claimed purpose, which makes it possible to conclude that the invention satisfies the criterion of industrial applicability.

According to the proposed invention, calculations were made concerning the method for operating the processing unit for producing a concentrate of aromatic hydrocarbons from natural gas.

The calculations are shown below.

Recycling hydrogen-containing gas in the pre-reforming stage makes it possible to raise the heat efficiency coefficient to 65%, which is a much higher than during conversion without recycling the hydrogen-containing gas, in which case the coefficient is 35-40%. Therefore, integrating the processes makes it possible to raise the heat efficiency coefficient by no less than 20%, which makes it possible to increase the yield by at least 40-50% of hydrocarbon raw material as a result of the conversion.

Recycling reduces the steam/carbon ratio (because of the presence of $H_2$ as well as $H_2O$ in the mixture to be converted, both of which hinder the formation of soot in reactors).

The scheme of the processing unit is simplified, wherein there is no need to mount an additional steam reformer or to use other schemes for correcting the composition of synthesis gas.

There is no need in the additional processing unit to separate hydrogen from hydrogen rich gas for the hydrogenation of sulfur-containing compounds in the desulfurization stage because the discharge gases from the synthesis of the concentrate of aromatic hydrocarbons can be used for this purpose. Gases with a high olefin content are hydrogenated at the hydrogenation step to $H_2S$.

The production yield of the concentrate of aromatic hydrocarbons is increased.

It is possible to synthesize highly concentrated crude methanol, which makes it possible to eliminate the step of concentrating same.

Additional Technical Result:

to increase the content of methylbenzenes including xylenes because, together with aromatization, a reaction occurs and the benzene rings undergo alkylation using methanol.

Thus, this invention solves the problem of interest which is to increase efficiency in the production of concentrates of aromatic hydrocarbons.

EXAMPLES

A mixture of desulfurized natural gas and discharge hydrogen-containing gas from the unit for synthesizing a concentrate of aromatic hydrocarbons from methanol is fed to the inlet of the unit for producing synthesis gas and recovering heat. The mixture is hydrogenated to remove the olefins and then mixed with superheated steam and heated to a temperature of 450-650° C. and fed to the autothermal reforming reactor (11). (T≈950° C., P—2-3 MPa). The steam-gas mixture from the reforming reactor (12) outlet is cooled and the condensed water therefrom is separated.

The unit for producing hydrogen from the discharge hydrogen-containing gas from the methanol synthesis: This unit can be composed of a processing unit for concentrating hydrogen which functions according to the principle of short-cycle absorption. The degree of extraction of hydrogen from the hydrogen-containing gas is 60%.

The crude methanol is synthesized along a circulation scheme from a compressed mixture of synthesis gas obtained in unit 1 with the addition of hydrogen obtained in the unit for producing hydrogen from discharge hydrogen-containing gas from synthesizing methanol.

The unit for synthesizing a concentrate of aromatic hydrocarbons from crude methanol.

The Unit for Producing Synthesis Gas by Means of the Technique of Autothermal Reforming and Heat Recycling.
Raw Material (Thousands of Metric Tons Per Year).

| | |
|---|---|
| Natural gas with methane equivalent 1.03 | −1000 |
| The discharge hydrogen-containing gas from synthesizing the concentrate of aromatic hydrocarbons | −378 |
| Water (steam) | −800 |
| Oxygen 99.5% | −1314 |
| Total: | −3491 |

Produced:

| | |
|---|---|
| Synthesis gas | −2834 |
| Condensed water | −657 |
| Total: | −3491 |

The Unit for Producing Hydrogen from Discharge Gases from Synthesizing Methanol
Raw Ingredient:

| | |
|---|---|
| Discharge gas from synthesizing methanol ($H_2$ −55 vol. %) | −356 |

Produced:

| | |
|---|---|
| Fuel gas from the unit for separating hydrogen | −336 |
| 99% hydrogen from the discharge gases from synthesizing methanol with extraction of 60% of the hydrogen | −20 |
| Total: | −356 |

The Unit for Synthesizing Crude Methanol (Circulation/Purge Ratio=20)
Raw Material:

| | |
|---|---|
| Synthesis gas | −2834 |
| 99% hydrogen | −20 |
| Produced: | −2854 |

| | |
|---|---|
| Crude methanol 94.5% | −2498 |
| Discharge hydrogen-containing gas | −356 |
| Total: | −2854 |

The Units for Synthesizing the Concentrate of Aromatic Hydrocarbons and for Separating the Conversion Product.
Raw Material:

| | |
|---|---|
| Crude methanol, 94.5 wt. % | −2498 |

Produced:

| | |
|---|---|
| Stabilized product (arene concentrate) Reid vapor pressure of 70 kPa | −663 |
| Reaction water, with 1.6 wt. % methanol | −1457 |
| Discharge hydrogen-containing gas | −378 |
| Total: | −2498 |

The Composition of Stabilized Product (Concentrate of Aromatic Hydrocarbons)

| | |
|---|---|
| Methanol | −0.04% |
| Aliphatic compounds | −2.64% |
| Benzene | −8.69% |
| Toluene | −35.69% |
| Aromatic hydrocarbons $C_8+$ | −40.10% |
| Aromatic hydrocarbons $C_9+$ | −12.84% |
| Total: | 100.00% |

The invention claimed is:

1. A method for producing a concentrate of aromatic hydrocarbons from natural gas, the method comprising:
   a) producing synthesis gas from natural gas;
   b) converting the synthesis gas into methanol;
   c) producing from the methanol, in the presence of a catalyst, a concentrate of aromatic hydrocarbons and water;
   d) separating the water from the concentrate of aromatic hydrocarbons and water;
   e) air stripping hydrocarbon residues from the water, thereby providing a concentrate of resultant aromatic hydrocarbons and a hydrogen-containing gas;
   f) using at least a portion of the hydrogen-containing gas in the production of the synthesis gas to adjust a ratio therein of $H_2$:CO to between 1.8-2.3:1;
      wherein the production of the concentrate of aromatic hydrocarbons and water from methanol in the presence of a catalyst, is carried out in two consecutively-connected reactors for synthesizing aromatic hydrocarbons:

(i) in a first isothermal reactor for synthesizing aromatic and aliphatic hydrocarbons;
(ii) in a second adiabatic reactor for synthesizing aromatic and aliphatic hydrocarbons from aliphatic hydrocarbons formed in the first reactor; and,
(iii) wherein the temperature of the second reactor is higher than the temperature of the first reactor;
wherein in a subsequent stabilization of the concentrate of resultant aromatic hydrocarbons in a stabilization unit there is provided a concentration of stabilized aromatic hydrocarbons; and,
wherein the at least a portion of the hydrogen-containing gas is fed to a synthesis gas production unit and is used for producing synthesis gas, wherein the synthesis gas production unit comprises: an autothermal reforming unit with a pre-reforming unit; the use of non-catalytic partial oxidation using oxygen or oxygen-air mixtures as the oxidant; or both, to adjust the molar ratio therein according to the relationship (the MF of $H_2$–the MF of $CO_2$)/(the MF of CO–the MF of $CO_2$)>2, where MF stands for the mole fraction of the component in the synthesis gas.

2. The method according to claim 1, wherein the reaction zone of the first reactor for synthesizing aromatic and aliphatic hydrocarbons is thermally stabilized by heating an external agent, wherein the heat is removed from the external agent by evaporating methanol in a methanol evaporator mounted between the unit for synthesizing methanol and the first isothermal reactor for synthesizing aromatic and aliphatic hydrocarbons.

3. The method according to claim 1, wherein aliphatic hydrocarbons removed from the concentrate of resultant aromatic hydrocabons in a conversion product separation unit are at least partially fed to a reaction zone of the first isothermal reactor for synthesizing aromatic and aliphatic hydrocarbons and/or to the reaction zone of the second adiabatic reactor for synthesizing aromatic and aliphatic hydrocarbons, which provides for an increase in the yield of the concentrate of aromatic hydrocarbons.

4. The method according to claim 1, wherein a catalyst based on a pentasil-type crystalline aluminosilicate with $SiO_2/Al_2O_3$=25-100 is used as the catalyst of the first isothermal reactor for synthesizing aromatic and aliphatic hydrocarbons, wherein the catalyst comprises 0.05-0.1 wt. % sodium oxide, 0.5-3.0 wt. % zinc oxide, 0.1-5.0 wt. % rare earth oxides, 0.05-2.5 wt. % cobalt oxide, 63.0-70.0 wt. % crystalline aluminosilicate, and a remainder being a binding component.

5. The method according to claim 1, wherein a catalyst based on a pentasil-type crystalline aluminosilicate with $SiO_2/Al_2O_3$=25-120 is used as the catalyst of the second adiabatic reactor for synthesizing aromatic and aliphatic hydrocarbons, wherein the catalyst comprises 0.05-0.1 wt. % sodium oxide, 0.5-3.0 wt. % zinc oxide, 0.12-0.30 sodium oxide, 0.1-3.0 wt. % rare earth oxides, 0.05-2.5 wt. % cobalt oxide, 63.0-70.0 wt. % crystalline aluminosilicate, and a remainder being a binding component;
wherein the composition of the rare earth oxides is:
$Nd_2O_3$: 21.%, and
$Pr_6O_{11}$: the remainder.

6. The method according to claim 1, wherein a portion of the hydrogen-containing gas produced in the process of synthesizing and separating the concentrate of aromatic hydrocarbons is used in a process of hydrogenating sulfur-containing compounds to hydrogen sulfide.

7. The method according to claim 6, wherein olefins which are contained in the produced hydrogen-containing gas are also hydrogenated together with the sulfur-containing compounds.

* * * * *